United States Patent [19]
Schookin et al.

[11] Patent Number: 6,161,038
[45] Date of Patent: Dec. 12, 2000

[54] NON-INVASIVE MONITORING OF HEMODYNAMIC PARAMETERS USING IMPEDANCE CARDIOGRAPHY

[75] Inventors: Sergei I. Schookin; Viatcheslav G. Zubenko; Konstantin R. Beliaev; Aleksandr A. Morozov, all of Moscow, Russian Federation; Wen H. Yong, Singapore, Singapore

[73] Assignee: Rheo-Graphic Pte Ltd., Singapore

[21] Appl. No.: 09/171,138

[22] PCT Filed: Apr. 7, 1997

[86] PCT No.: PCT/SG97/00013

§ 371 Date: Oct. 8, 1998

§ 102(e) Date: Oct. 8, 1998

[87] PCT Pub. No.: WO97/37591

PCT Pub. Date: Oct. 16, 1997

Related U.S. Application Data

[63] Continuation of application No. 08/629,420, Apr. 8, 1996, Pat. No. 5,685,316.

[51] Int. Cl.⁷ ........................................ A61B 5/04
[52] U.S. Cl. .................... 600/519; 600/509; 600/513
[58] Field of Search ................. 600/508, 513, 600/519

[56] References Cited

U.S. PATENT DOCUMENTS

| | | |
|---|---|---|
| 3,340,867 | 9/1967 | Kubicek et al. . |
| 4,016,868 | 4/1977 | Allison . |
| 4,450,527 | 5/1984 | Sramek . |
| 4,458,694 | 7/1984 | Sollish et al. . |
| 4,781,201 | 11/1988 | Wright et al. . |
| 4,807,638 | 2/1989 | Sramek . |
| 4,836,214 | 6/1989 | Sramek . |
| 4,854,327 | 8/1989 | Kunig . |
| 4,953,556 | 9/1990 | Evans . |
| 4,979,110 | 12/1990 | Albrecht et al. . |
| 5,046,502 | 9/1991 | Kunig . |
| 5,178,154 | 1/1993 | Ackmann et al. . |
| 5,261,411 | 11/1993 | Hughes . |
| 5,265,615 | 11/1993 | Frank et al. . |
| 5,309,917 | 5/1994 | Wang et al. . |
| 5,402,795 | 4/1995 | Reichl . |
| 5,406,955 | 4/1995 | Bledsoe et al. . |
| 5,423,326 | 6/1995 | Wang et al. . |
| 5,469,859 | 11/1995 | Tsoglin et al. . |
| 5,503,157 | 4/1996 | Sramek . |
| 5,505,209 | 4/1996 | Reining . |

FOREIGN PATENT DOCUMENTS

| | | |
|---|---|---|
| WO 84/00227 | 1/1984 | WIPO . |
| WO 89/01312 | 2/1989 | WIPO . |
| WO 93/04627 | 3/1993 | WIPO . |

OTHER PUBLICATIONS

Arinchin, V.I. et al. "Taking Into Account Electrical Resistance of Blood Will Increase Accuracy of Chest Tetrapolar Rheography Method", Pediatric (SU Journal), 1987, N7, p. 59–62.

International Search Report, dated Aug. 18, 1997 (3 pages).

Primary Examiner—Carl H. Layno
Attorney, Agent, or Firm—Trask Britt

[57] ABSTRACT

A method and apparatus for determination of heart rate, heart stroke volume, heart stroke volume, and cardiac output from thoracic bioimpedance signals and electrocardiograms. A unique bioimpedance electrode arrangement is employed, and the bioimpedance signals are corrected for gain-phase-frequency distortion through the use of sinusoidal test signals through the measuring or detection electrodes to identify distortions and correct for same during actual measurements. Time-derivative bioimpedance signals are employed, the power spectrum calculated, and a novel autoconvolution procedure used to emphasize the heart rate harmonic. Breath waves and other signals not indicative of the patient's cardiocycles are removed. Left ventricular ejection time is derived from the bioimpedance signals, and an improved version of Kubicek's equation is employed to derive heart stroke volume and thus cardiac output.

67 Claims, 10 Drawing Sheets

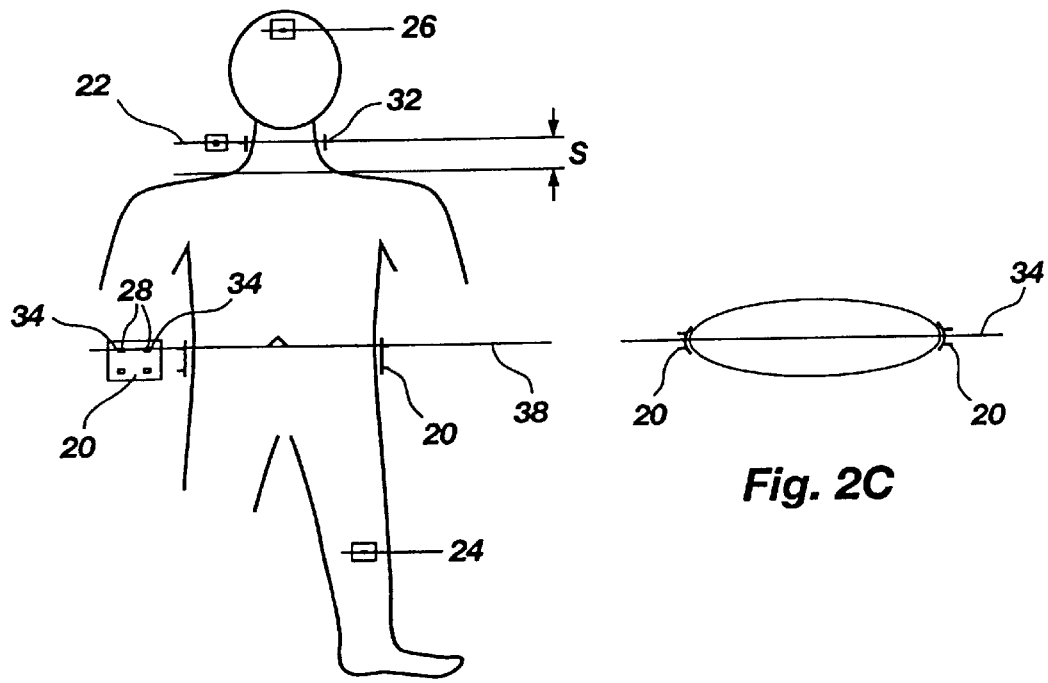
Fig. 2B
Fig. 2C
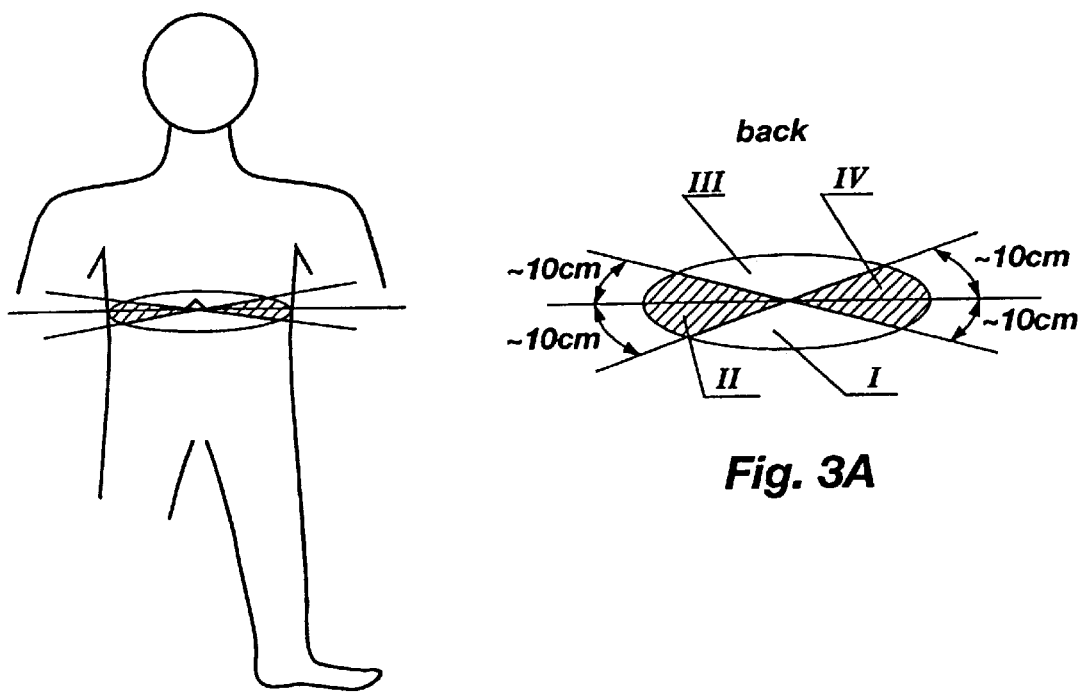
Fig. 3B
Fig. 3A

NON-INVASIVE MONITORING OF HEMODYNAMIC PARAMETERS USING IMPEDANCE CARDIOGRAPHY

This application is a continuation of Ser. No. 08/629,420 filed Apr. 8, 1996 now U.S. Pat. No. 5,685,316.

TECHNICAL FIELD

The present invention relates generally to cardiac monitoring and specifically to the determination of heart rate (HR), heart stroke volume (SV), and cardiac output (CO) according to detection and complex analyses of thoracic bioimpedance and electrocardiograph (ECG) signals, which permit precise detection of the start of left ventricular ejection.

BACKGROUND ART

Heart rate is the number of times the heart beats per minute. Heart stroke volume is the volume of blood pumped during each heart stroke. Cardiac output is the volume of blood pumped in one minute and is generally considered to be the most significant gauge of cardiac fitness. Physicians must frequently rely upon such cardiac parameters to diagnose heart disease, to assess a patient's overall health, to determine the most appropriate method of treatment, and to quickly discover sudden lapses in cardiac performance.

The currently existing methods for measuring cardiac output and other cardiac parameters may be divided into two categories: invasive and noninvasive. The invasive methods require that a medical practitioner insert a measuring device into the patient's body, such as a catheter in the throat, and present numerous disadvantages to both patient and physician. The patient must often endure substantial pain and discomfort and the physician must perform a relatively complicated procedure and occasionally expose himself or herself to the risk of contact with infectious blood. The noninvasive methods currently in use represent a major advancement, but still have significant shortcomings. Most take measurements using ultrasound, phonocardiography, or electrical bioimpedance in order to calculate cardiac parameters.

The methods which employ bioimpedance measurement involve placing a plurality of electrodes on a patient's skin (predominantly in the thoracic region), generating a high frequency, low amplitude electric current from certain of the electrodes into the patient's body, measuring the changes in the electrical impedance of the patient's tissue over time, and correlating the changes in electrical impedance with cardiac parameters.

The manner of arranging the electrodes on the patient's body plays an important part in the relative accuracy of the ultimate cardiac parameter measurements. Due to various anatomical factors, electrodes must be placed over certain areas of the body to achieve optimum correlation between measured changes in bioimpedance and cardiac parameters. Many of the electrode configurations currently in use fail to adequately take into account the paths followed by the lines of electrical potential through the thorax and thus create a distortion in the cardiac measurement. Moreover, a few electrode arrangements require the use of band electrodes, e.g., influencing band electrodes A, B and measuring band electrodes C, D each having a width "n" (see FIG. 1). These band electrodes typically wrap around a patient like a belt and further limit access to the patient, an especially undesirable condition curing reanimation procedures. The movements associated with respiration also make band electrodes very inconvenient when placed on the neck and chest.

Perhaps the most significant problem with the presently existing bioimpedance methods in the imprecise mathematical derivation of cardiac parameters from bioimpedance measurements. The ventricular ejection time (VET) is a measurement of the time between the opening and closing of the aortic valves during the systole-diastole cycle of the heartbeat and it must be calculated as an intermediate step in determining cardiac stroke volume. The prior art does not teach a method for determining ventricular ejection time with sufficient accuracy. Furthermore, the prior art fails to account for the fact that VET is not a single event. In reality, there is actually a left VET and a right VET. It has been shown that the time-derivative impedance signal is actually proportional to the peak aortic blood flow ejected by the left ventricle. The measurements of left VET and right VET for most patients are generally very close, but even slight differences between them can create errors in bioimpedance readings under the methods currently in use.

Furthermore, the classic algorithm for ejection start time is elaborate, and works well only for healthy patients at rest. It is not accurate for patients under physical training or other physical stress, or for critically ill patients, such as those typically in intensive care units.

The conventional equation for deriving stroke volume from bioimpedance signals has become known as the Kubicek equation and is given as follows:

$$SV = R(L/Z_0)^2 \cdot \Delta Z$$

where SV is heart stroke volume, R is blood resistivity, L is the distance between the inner and outer voltage sensing electrodes, $Z_0$ is the mean thoracic impedance determined from the inner voltage sensing electrodes, and $\Delta Z$ is the impedance change due to blood influx. Kubicek's estimation of this value is $$\Delta Z = (VET) \cdot (dZ/dt)_{max}$$

where VET is the combined left and right ventricular ejection time, and $(dZ/dt)_{max}$ is the maximum negative slope change of the time-differentiated impedance signal. Most bioimpedance cardiac monitoring systems use some form of the Kubicek equation.

Without further refinement, however, the Kubicek equation frequently given inaccurate measurements. This is due in part to the fact that both ventricles contribute to impedance changes, and so Kubicek's calculated ejection time (VET) cannot be associated with a particular, specifically the left, critical ventricle. Concurrently, Kubicek's $\Delta Z$ estimation becomes invalid when strong left-right ventricles asynchronism is observed. As a result, Kubicek's SV calculation is often proportional to, but not equal to, the actual heart stroke volume and must therefore be multiplied by some correlating constant. In addition, the prior art does not disclose a method for adjusting R in accordance with the fluctuation of a patient's hematocrit (red blood cell count). The adjustment of R is especially important in patients undergoing blood infusion.

Many of the methods for bioimpedance cardiography require that the patient hold his or her breath during each measurement because respiration causes interference in the bioimpedance signal. Such methods are inconvenient for some patients and completely useless for other patients who are unconscious or otherwise unable to hold their breath. Some of the more recent methods include signal processing capability to enhance the signal, to identify the effects of respiration, and to eliminate defective signals to that errors are not introduced into the final calculations. Effective signal processing is generally the key to insuring accuracy in bioimpedance cardiography and improvements in this are can represent significant advances in the art.

DISCLOSURE OF INVENTION

The invention discloses a method of measuring hemodynamic parameters using a novel combination of bioimpedance cardiography and electrocardiography which allows medical practitioners to obtain an accurate, substantially continuous assessment of a patient's cardiac performance. The bioimpedance and electrocardiogram signals are measured over a common time interval of interest, preferably more than ten (10) heartbeats.

The apparatus of the invention uses a series of spot electrodes adapted for placement on the surface of the patient's skin to generate a high frequency, low amplitude electrical current through the thorax of the patient and to measure changes in the bioimpedance. The disclosed electrode configuration takes advantage of the physiological arrangement of electrical potential power lines in the body.

Concurrently, a method of the invention may utilize electrocardiography to enhance the accuracy of the ejection time detection from the measured bioimpedance signal. The electrocardiogram can be obtained in any standard position, well known in electrocardiography. To eliminate the overall quantity of electrodes at the patient's skin, this invention may use the same set of electrodes for bioimpedance and ECG measurements (see FIG. 6B).

The invention may also involve the step of continuously adjusting the calculation of cardiac parameters according to changes in the red blood cell count and according to varying bodily compositions of different patients, and can thus be used under a variety of different circumstances without a loss of accuracy.

In addition, the invention comprises a method of improved bioimpedance signal processing. It may employ a computer system to analyze the both the bioimpedance signal and the electrocardiogram in a variety of ways to provide an accurate report of cardiac parameters. The computer system may be used to make corrections in the gain-phase-frequency characteristics caused by the transducers used to measure the bioimpedance and ECG. The computer system communicates a sinusoidal test curve to the transducer receiver and may then measure and record the gain-phase-frequency distortions created by the receiver. The "real" bioimpedance signals subsequently received by the computer system through that transducer may pass through filters which remove the transducer's characteristic distortions as well as breath and movement artifacts. Accuracy of gain-frequency response and phase-frequency response may be corrected to within 5%.

The invention may further comprise a method of signal processing the BCG signal to determine QRS complexes (characteristic heartbeat waveforms) and check point positions for use in refining the bioimpedance signal calculations. The signal processing may involve sampling the measured ECG signal and filtering it to highlight the positions of the QRS complexes. Peak-to-peak amplitudes may be recorded and a threshold amplitude may be calculated. Defect-free QRS complexes are selected using the threshold amplitude. Finally, additional analysis of selected events may be performed to determine check point positions.

The computer system of the invention may derive and save in memory a time-derivative bioimpedance signal. The curve generated by the time-derivative bioimpedance signal may be plotted with respect to time and represents repeated cardiocycles. The power spectrum of the bioimpedance signal may be calculated with discrete Fourier transforms and studied to estimate the patient's heart rate and to identify the fronts of each cardiocycle. A novel mathematical autoconvolution procedure may be used to emphasize the heart rate harmonic in the time-derivative bioimpedance signal.

Breath waves may be removed by generating an envelope within the power spectrum in which cardiocycle signals should be found and then removing those signals which lie outside the envelope.

The computer system may employ a new method of deriving the effective left ventricular ejection time (ELVET) from bioimpedance signals and ECG signals. In particular, precise detection of the ejection start time is based on complex analyses of the bioimpedance and ECG signals. The derivation of ELVET is a detailed, multi-step analysis which involves finding various points on the time-derivative bioimpedance curve based on corresponding points on the ECG curve and determining which of these points most accurately reflect cardiac events. It requires making a variety of mathematical calculations, including making approximations for differentials of the time-derivative bioimpedance curve.

In healthy patients there is very little left-right ventricular asynchronism or asynchronism between opening of left and right ventricle valves. However, in seriously ill patients, the Kubicek equation generally underestimates the time-derivative bioimpedance signal due to left-right ventricular asynchronism. The computer system, in accordance with the invention, automatically adjusts for signals which exhibit asynchronism between opening of left and right ventricle valves to calculate the correct value of $\Delta Z$, the impedance changes due to blood influx.

After the computer system calculates ELVET and $\Delta Z$, it employs an improved form of Kubicek's equation to derive Heart Stroke Volume from ELVET, blood resistivity, the patient's specific body constitution, and the maximum bioimpedance change. The computer system analyzes the time-derivative bioimpedance signal to eliminate cardiocycles with certain aberrations.

Finally, the invention further comprises a method of detecting valid cardiocycles.

BRIEF DESCRIPTION OF DRAWINGS

FIGS. 2A, 2B, and 2C schematically depict spot-type electrode placements according to the present invention;

FIG. 3A depicts anatomical zones of interest for placement of measuring chest electrodes according to the present invention;

FIG. 3B illustrates the positioning of the anatomical zones of FIG. 3 on a patient;

Figure 7B:
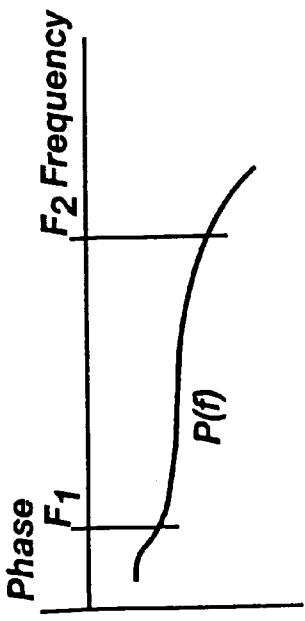
FIG. 7A depicts the gain-frequency characteristic G(f) of a bioimpedance transducer according to the present invention.
FIG. 7C depicts the gain frequency characteristic $$\frac{1}{G(f)}$$
Figure 7D:
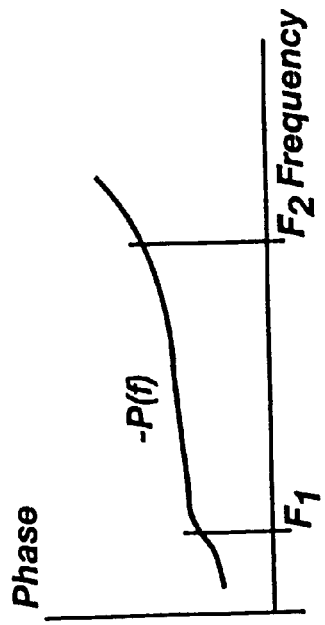
Figure 7A:
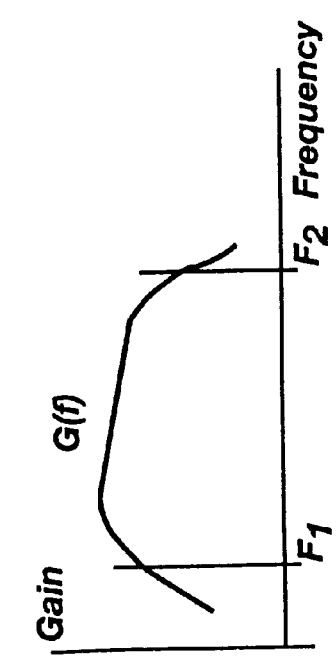
Figure 7C:
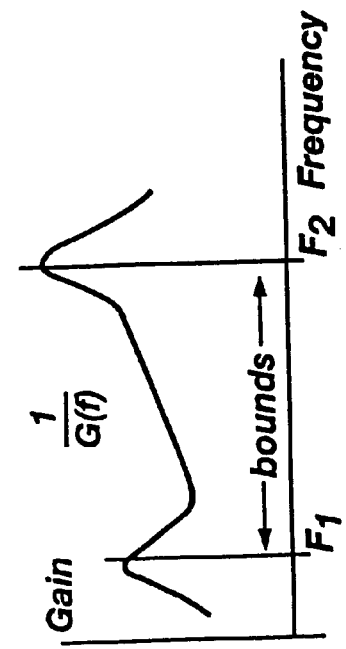
Figure 8A:
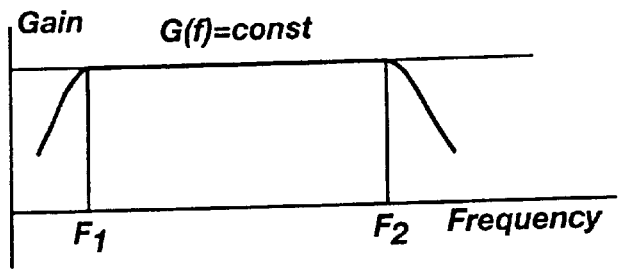
Figure 8B:
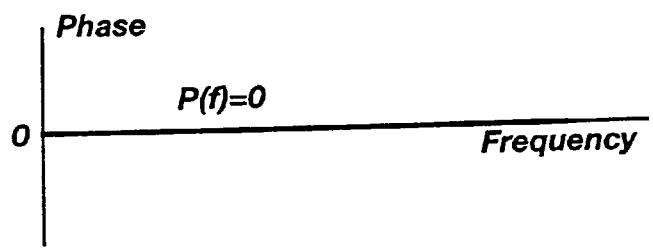
Figure 9:
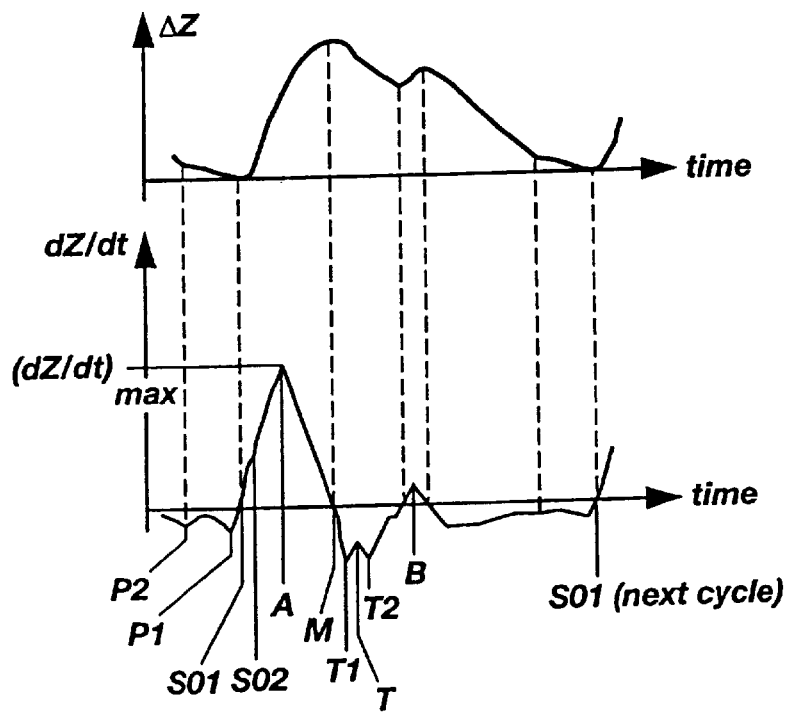
Figure 10:
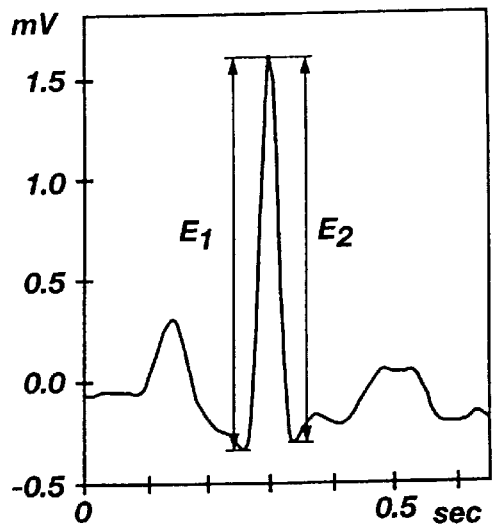
Figure 11:
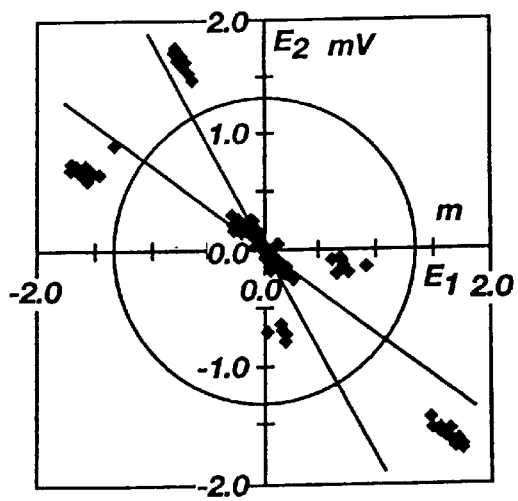
Figure 12:
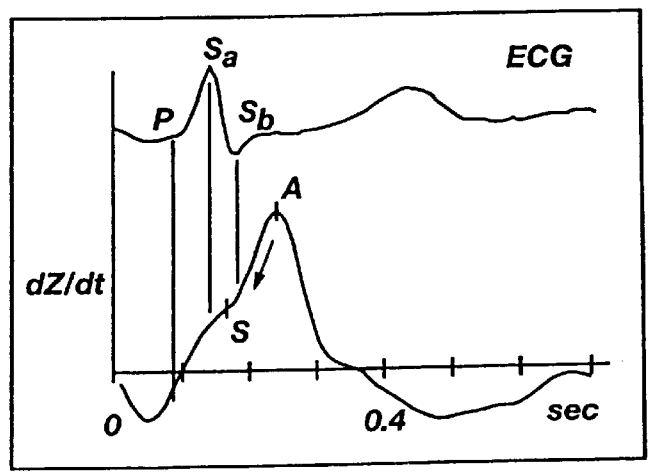
Figure 13:
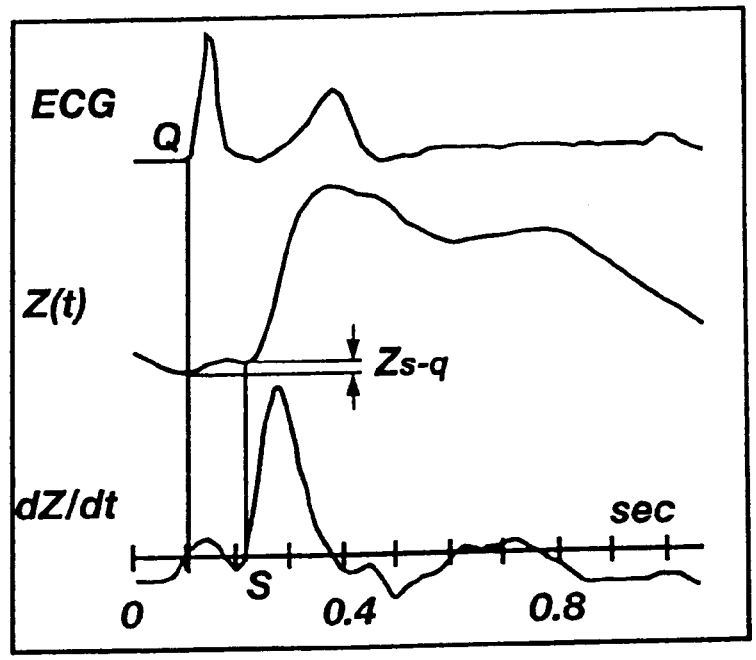
Figure 14:
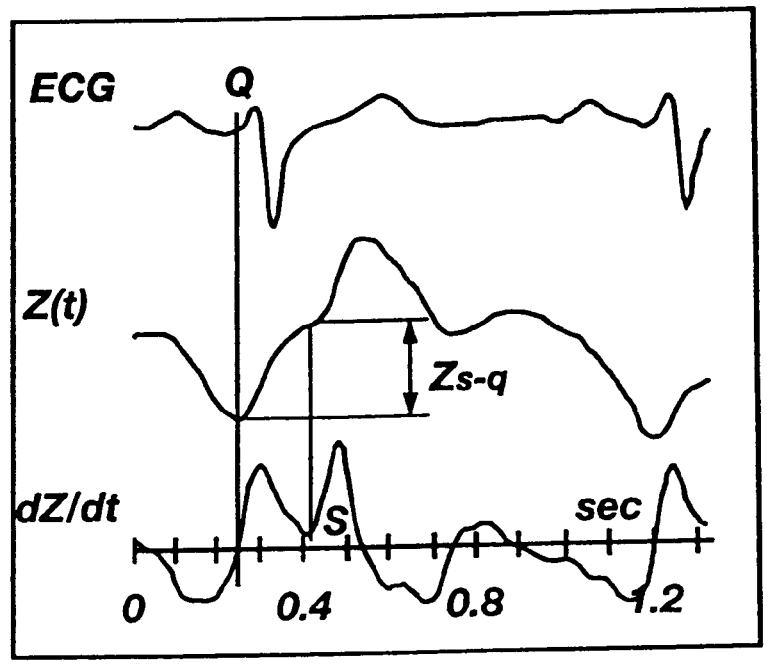
Figure 15:
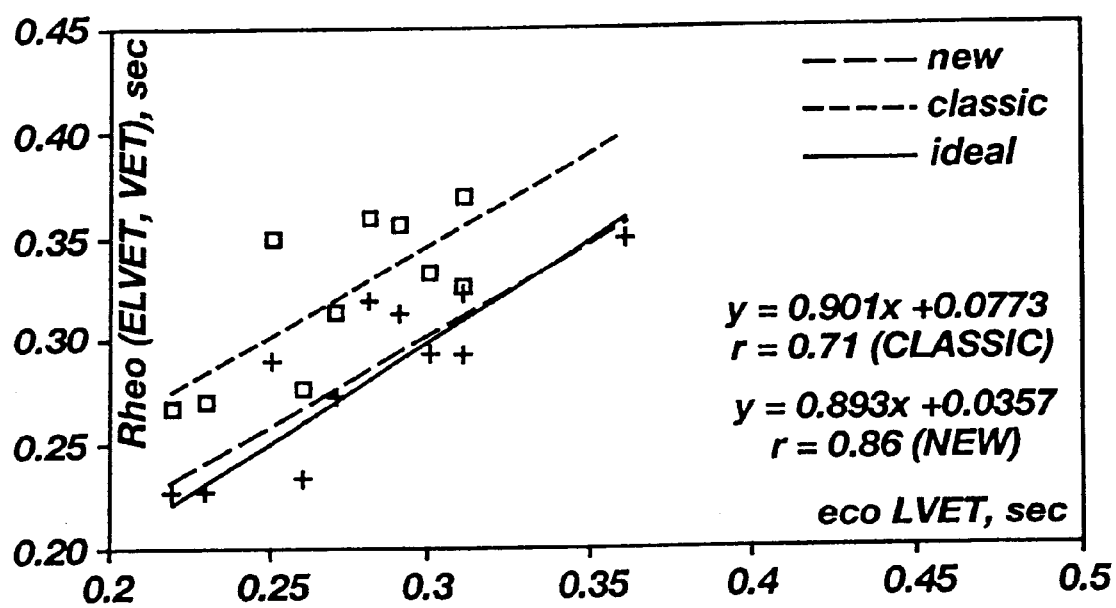

of an "R" or restoring filter corresponding to the characteristic of FIG. 7A as used for GPF corrections according to the instant invention;

FIG. 7D depicts the phase frequency characteristic —P(f) of an "R" or restoring filter corresponding to the characteristic of FIG. 7B as used for GPF corrections according to the instant invention;

FIG. 8A depicts the resulting gain frequency characteristic G(f) of a transducer signal as corrected by an R-filter according to the present invention;

FIG. 8B depicts the resulting phase frequency characteristic P(f) of a transducer signal as corrected by an R-filter according to the present invention;

FIG. 9 is an illustration of a time-derivative bioimpedance signal generated according to the present invention, plotted with respect to time and depicting exemplary impedance changes due to blood influx ($\Delta Z$) over the same time period;

FIG. 10 is a graph of the electric potential traversing the heart of a patient plotted with respect to time (electrocardiogram), depicting the peak-to-peak amplitudes ($E_1$—Front, $E_2$—back) of the QRS complex in a single heartbeat;

FIG. 11 is a scatter diagram of all peaks measured in an electrocardiogram over a period of ten seconds. The coordinates of the graph are ($E_1$, $E_2$), and the QRS complexes are within the dotted circle in the lower right hand corner;

FIG. 12 is a graph of the ECG signal and the time-differentiated bioimpedance signal plotted against time indicating check-points, P, $S_a$, and $S_b$ on the ECG signal, relative to check-points, Q, S, and A on the time-differentiated bioimpedance signal;

FIG. 13 is a graph of ECG, bioimpedance Z(t), and time-differentiated bioimpedance dZ/dt, signals with respect to time indicating the bioimpedance difference between the S and Q points, $Z_{s-q}$ in a healthy patient;

FIG. 14 is a graph of ECG, bioimpedance Z(t), and time-differentiated bioimpedance dZ/dt, signals with respect to time indicating the bioimpedance different between the S and Q points, $Z_{r-q}$ in a patient with ischemic heart disease; and FIG. 15 is a graphic depiction of the correlation of the inventive method of determining ELVET to an ideal, ultrasound determination in comparison to the classic Kubicek algorithm methodology.

BEST MODES FOR CARRYING OUT THE INVENTION

The first step in the present invention involves taking bioimpedance measurements over segments of tissue on a patient's body. Electrodes must be placed at appropriate points on the surface of the skin to generate a high frequency, low amplitude electric current and to detect changes in the generated current after it passes through the segments of tissue (see FIGS. 2A, 2B, 3 and 4). The electrodes are "spot electrodes" rather than "band electrodes" in order to maximize the free area on the patient's body. The spot electrodes are preferably of the disposable, one-use type. The patient thus has increased freedom of movement and medical practitioners have more access to the patient's skin for other medical procedures, such as the introduction of catheters and the administration of anesthesia.

The bioimpedance electrode system employs a total of six electrodes: a pair of detecting (measuring) electrodes 20 at the xiphoid process level, a pair of detecting (measuring) electrodes 22 positional laterally on the neck, an influencing electrode 24 on the left leg, and an influencing electrode 26 on the forehead.

The influencing electrodes 24, 26 may be standard ECG spot electrodes with a contact area of 2 centimeters by 2 centimeters (cm). The upper influencing electrode 26 is preferably placed on the middle of the forehead, at the mid-line thereof. The lower influencing electrode 24 is preferably placed on the left knee or somewhere below the left knee such as the left floor. If necessary, the lower influencing electrode 24 may also be placed above the knee level, provided that the following condition is satisfied:

$$L > 5R,$$

where L is the distance between influencing electrodes and R is the radius of the chest. The left leg is used instead of the right leg to account for the anatomic asymmetry of the heart. The physiological positioning of the aortic arch, through which is a significant concentration of electrical potential power lines pass, makes the left leg most suitable for the lower influencing electrode. The arrangement of influencing electrodes in this manner guarantees the uniform distribution of influencing current power lines between measuring electrodes and thus helps to minimize the error in the final cardiac parameter measurements.

The upper pair of measuring electrodes may also be standard ECG spot electrodes with a contact area of 2 cm by 2 cm. These electrodes are placed symmetrically along the lateral lines of the patient's neck about the perimeter of the patient's neck 27, a distance S above the base of the neck. The distance S is defined as the distance between the base of the neck and the center 302 of electrode 22 and is preferably approximately 4 cm. The base of the neck is defined to be located at the point of maximum curvature of the lateral lines of the neck. Placing the upper measuring electrodes 22 in this area avoids the error that would otherwise result from the nonlinearity of electrical power lines at the neck-chest junction.

The lower chest pair of measuring electrodes 20 each have a contact area of 12 $cm^2$ to 30 $cm^2$. If this contact area is either reduced or enlarged, the heart stroke volume will be underestimated. A contact area of less than 12 $cm^2$ provides insufficient depth of measurement, a particularly serious problem with large patients, and a contact area of more than 30 $cm^2$ causes the measurement to extend into additional anatomical regions.

Figure 1:
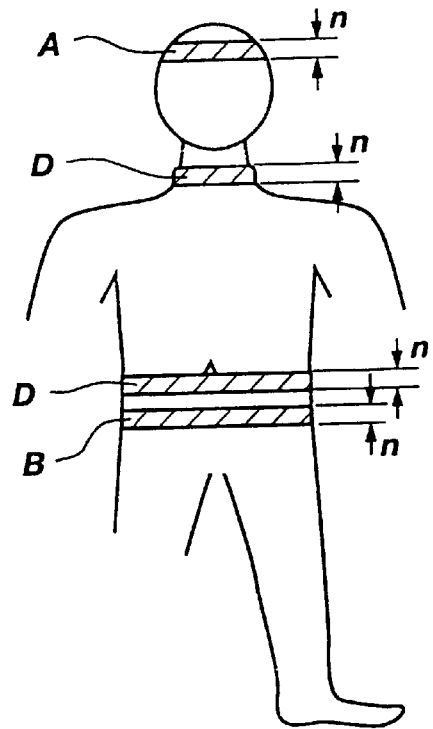
FIG. 1 is a schematic depiction of a band-type electrode arrangement on a patient.
Figure 2A:
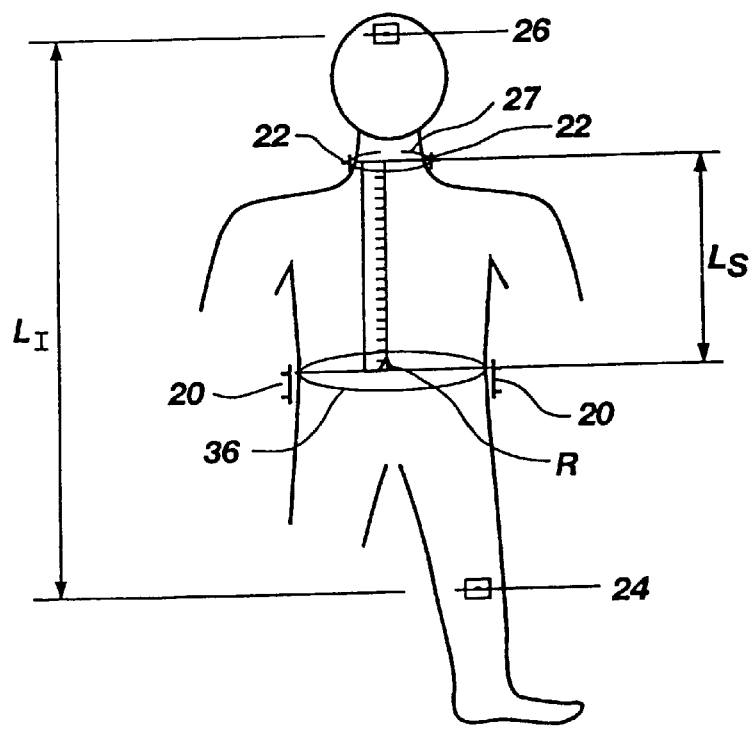
Figure 4:
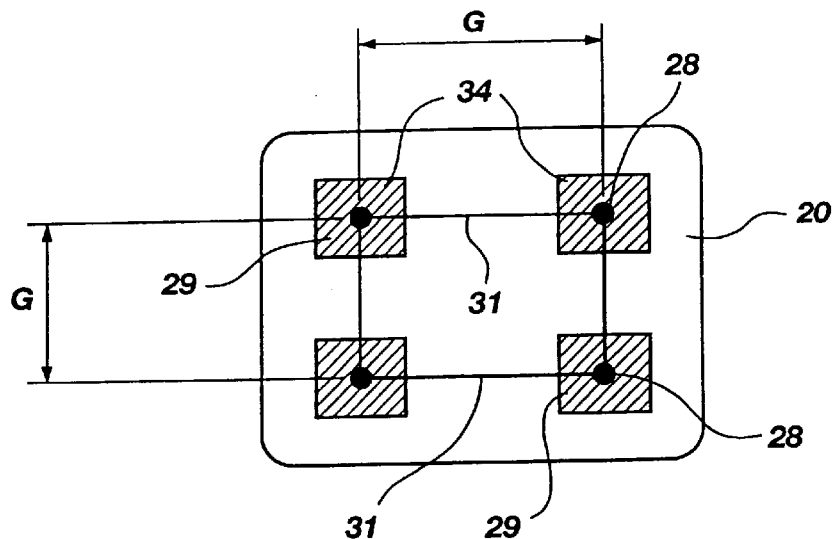
FIG. 4 illustrates the structure of an individual chest electrode according to the present invention.

The individual chest electrodes 20 are each preferably comprised of a set of four standard ECG spot electrodes 28, each with a contact area 29 of 2 cm by 2 cm with the top pair 34 of spot electrodes 28 of each chest electrode at xiphoid process level 38 (see FIGS. 2B and 4). All contact areas 29 are connected with foil or wire 31. The distance G separating adjacent spot electrodes is approximately 5 cm. The contact areas 29 are placed on the body using a conductive gel, if not an integral feature of the spot electrodes 28. Such a design takes advantage of the anatomic features of zones I and III of the body (see FIGS. 3A and 3B) and insures a minimum of error since the measurement is taken at an adequate depth and allows for variations in the bodily constitutions of different patients. The chest electrodes 20 as described are placed laterally on opposite sides of the chest (see FIGS. 2A, 2B, and 2C) at the xiphoid process level 38. As shown in FIGS. 3A and 3B, placement is in zones II and IV, within an area anteriorly or posteriorly plus or minus about 10 centimeters of a lateral line extending through the body at xiphoid process level 38.

The influencing electrodes 24, 26 generate a high frequency, low amplitude current into the patient's body and the detecting electrodes 20, 22 measure the current after it passes through body tissue. The electrical impedance of the tissue can readily be determined from the difference between the generated current and the measured current. The electrical impedance of tissue varies over time as a result of blood flow, respiration, and other factors.

The present invention also uses ECG signals concurrently measured with the bioimpedance signals. With the exception of post-measurement signal proceeding to remove hardware artifacts described below, the ECG signal measurement is performed in a conventional manner, and so will not be further described.

A preliminary step in the present invention is to determine the gain-phase-frequency (GPF) characteristics of the analog input devices (ECG converter and impedance converter) for subsequency use in signal processing.

A computer system, which may comprise a specifically programmed general purpose computer such as a personal computer, receives the electrical current measurements from the detecting electrodes 20, 22, determines both the impedance of the interceding tissue (bioimpedance) and the electric potential traversing the heart (ECG) as a function of time, and ultimately calculates HR (heart rate), SV (heart stroke volume), and CO (Cardiac Output). The equation for determining SV is given as follows:

$$SV = K \cdot P \cdot (L/Z_0)^2 \cdot \Delta Z$$

where K is a novel scale factor, P is the specific blood resistivity, L is the distance between the voltage measuring or sensing electrodes 20 and 22, $Z_0$ is the mean or base thoracic impedance (determined from sensing electrodes 20 and 22) and $\Delta Z$, the impedance changes due to blood influx. $\Delta Z$ is calculated as $$\Delta Z = \text{ELVET} \cdot (dZ/dt)_{max} + Z_{s-q},$$

where ELVET is the effective left ventricular ejection time, $(dZ/dt)_{max}$ is the maximum absolute value of the time-differentiated impedance signal obtained from the two measuring electrodes, and $Z_{b-q}$ is a novel correction factor that takes into account left-right ventricles asynchronism, equal to the bioimpedance difference between S and Q points (see FIGS. 13 and 14 and accompanying text).

The K term accounts for variations in body compositions of different patients. In order to obtain a value for the K factor, the medical practitioner first measures the height and weight of the patient and the perimeter of the patient's neck 27 and chest 36 using conventional means or commercially available ultrasonic measuring means. The medical practitioner then inputs these values into the computer system, which in turn uses the values to compute the effective cross-sectional area of the chest and the K factor. The effective cross-sectional area of the chest (SCHEST) is given by:

$$\text{SCHEST} = (\text{PCHEST}^2 + (\text{PNECK} \cdot \text{PCHEST}) + \text{PNECK}^2)/12\pi,$$

where PCHEST is the perimeter of the patient's chest 36 and PNECK is the perimeter of the patient's neck 27. Then the K factor is calculated as follows:

$$K = K_0 - K_1 \cdot (\text{SCHEST}/(H^{K_2} \cdot W^{K_3})),$$

where H is the patient's height, W is the patient's weight, and $K_0$, $K_1$, $K_2$, $K_3$ are gender and age dependent and lie in ranges:

$$K_0 \in [1-4]; K_1 \in [3-16]; K_2 \in [0-1]; K_3 \in [0.1-2]$$

The present invention can thus be used on patients of varying body constitutions without a loss of accuracy.

The electrical resistivity of human blood is not a constant. It varies among different individuals and even in the same individual at different times. Blood resistivity is particularly susceptible to fluctuations in patients undergoing blood infusion. As a result, an accurate system of bioimpedance cardiography must include means for continuously modifying the blood resistivity term of the Kubicek equation.

A patient's specific blood resistivity depends largely upon his or her hematocrit. The relationship between these two values for capillary blood is as follows:

$$P = 13.5 + 4.29 \cdot H$$

where P is the specific blood resistivity and H is the capillary hematocrit. This relationship is adopted from V. I. Arinchin et al., "Taking into account electrical resistance of blood will increase accuracy of chest tetrapolar rheography method," Journal of Pediatrics (U.S.S.R.) 1987, v. 7, pp. 59–52. The hematocrit can be measured using any commercially available method. It may either be inputted into the computer system by the medical technician, or sent by electronic means directly from the hematocrit measuring device.

The invention utilizes a novel method for processing the ECG signal, (after hardware artifact removal) comprised of the following steps:

(i) signal approximation from sampling points, (ii) special filtering to highlight the positions of QRS complexes, (iii) measuring peak-to-peak amplitudes for a given, recorded time interval, (iv) calculation of amplitude threshold, (v) QRS selection with the calculated amplitude threshold, (vi) additional analysis of selected events to determine check point positions.

Step (i) above is desirable to increase the accuracy and reliability of QRS determination unless sampling frequency in extremely high. As a matter of practicability, such high frequency sampling is undesirable as consuming excessive processing time and memory capacity, and is impractical to effectuate the signals of restricted power spectrum. It is contemplated that two approaches to approximation may be suitable for use with the invention. First, it is well known that any signal s(t) with finite spectrum (and defining the highest harmonic as $\omega_m = 2\pi f_m$), is fully described by its samples at points $s(n \cdot \Delta T)$, where $\Delta T \leq \frac{1}{2} f_m$ is the sampling period, and n is an integer. A precise approximation of such a signal is given by the equation:

$$s(t) = \sum_{n=-\infty}^{\infty} s(n \cdot \Delta T) \frac{\sin \pi \cdot \left(\frac{t}{\Delta T} - n\right)}{\pi \cdot \left(\frac{t}{\Delta T} - n\right)} = \sum_{n=-\infty}^{\infty} s(n \cdot \Delta T) \varphi_n(t)$$

$$\text{where } \varphi_n(t) = \text{sinc}\left(\pi \cdot \left(\frac{t}{\Delta T} - n\right)\right).$$

The same result can be obtained in another way by first calculating a Fourier transform of the signal s(t) and adding a small phase shift Δϕ, to all harmonics, to that $$\Delta\phi/2\pi f = \tau = \text{const}, \forall f.$$

Then, after calculation of the inverse Fourier transform, the approximated values of s(t) at the points shifted by τ from the original samples are obtained. This latter approach is more efficient in calculation. Both methods permit lower sampling rates that leas to less consumption of memory and can be employed on demand to calculate a precise approximation of the original signal.

The next step is filtering the ECG signal to highlight the positions of QRS complexes. FIG. 10 illustrates a typical QRS complex, a signal peak with greatest amplitude measured from peak-to-peak in a single heartbeat. A symmetrical finite impulse response (FIR) digital filter is calculated from the desired gain-frequency characteristic (FGC$_{filter}$). The desired GFC$_{filter}$ is elaborated from analysis of power spectrum of QRS complexes and has a passband from 6 Hz to 22 Hz with the maximum at 12.5 Hz. Using a discrete Fourier transform, the desired GFC$_{filter}$ is converted to finite impulse characteristic according to an algorithm for filter synthesis described in V. S. Gutnikov, "Filtration of measured signals," Leningrad, Energoatomizdat (USSR) 1990, pp. 172–181, incorporated herein by reference. This filter passes the QRS complexes and suppresses breath and movement artifacts in the ECG signal, also as P and T waves.

The next step is to calculate the peak-to-peak amplitude threshold and select valid QRS complexes. The computer system measures each local peak of the filtered ECG signal by its front ($E_1$) and back ($E_2$) amplitude fronts, see FIG. 10. For each local peak, $E_1$ is the measured from the peak's anterior, or leading local minimum to the next nearest maximum, and $E_2$ is measured from the peak's anterior, or leading local minimum to the next nearest maximum, and $E_2$ is measured from the peak's maximum to its posterior, or trailing, minimum. FIG. 11 depicts a distribution (scatter diagram) of peaks by their ($E_1$, $E_2$) coordinates for a time interval or period of 10 seconds. FIG. 11 also shows the QRS complexes highlighted within a dotted circle in the lower right hand corner of the figure. Each peak is characterized by its ($E_1$, $E_2$) vector and amplitude $A_i$, where $$A_i = ((E_{1i})^2 + (E_{2i})^2)^{1/2}.$$

The computer system then searches the sorted $\{A_i\}$ array for the maximum difference between $A_i$ and $A_{i+j}$. If the maximum is found for an exemplary k-th element, then the amplitude threshold is calculated as $T=(A_i+A_{k+j})/2$. Thus, the QRS complex is detected in point j if $A_j$ exceeds the threshold T. The threshold T is adapted for each 10 second block or interval of ECG data as $T_a = T_{ak-1} + \alpha T_k$, where $T_{ak-1}$ is the adapted threshold for the previous data block, $T_k$ is the calculated threshold for the current block, and α is a parameter of adaptation in the range of 0–1.

Each QRS complex identified by the use of the above "threshold" methodology is then further analyzed within an interval of −50 to +200 milliseconds (ms) from the determined QRS position. For each QRS complex identified, the computer system determines the amplitude, sequence of peaks, and derivative of peak fronts to arrange 3 check points (FIG. 12): the start of the QRS complex (P-point), the maximum derivation from the base-line ($S_a$-point, which coincides with peak R in a normal ECG), and the end of the QRS complex ($S_h$-point). These check points are used to refine the analysis of the bioimpedance signal described below.

The invention utilizes a novel method for processing the bioimpedance signal comprised of the following steps:

(i) digital filtration and phase correction,
(ii) heart rate estimation,
(iii) suppression of breath waves,
(iv) determination of cardiocycles,
(v) arrangement of check points, and
(vi) selection of cycles without interference artifacts.

The first part of the electronic filtration involves passing the signal through a "restoring" R-filter to achieve gain-phase-frequency (GPF) correction. The R-filter compensates for the distortions caused by the particular electronic transducer that is used to measure bioimpedance changes. It is well known that GPF characteristics of a bioimpedance transducer (FIG. 7) may greatly influence the shape of the bioimpedance curve. These interferences must be removed from the signal. The R-filter uses posterior signal processing to correct linear GPF distortions. It is constructed in such a way that the system of the bioimpedance transducer plus R-filter has GPF characteristics with zero phase shift and constant gain at the given range of frequencies, for example from 0.3 Hz to 30 Hz for the bioimpedance signal (see FIG. 8). Thus, correlation of the outputs of different bioimpedance devices may be achieved. With the exception of the filter parameters and operating characteristics specified as desirable or critical for the R-filter and other filters described herein, construction of same is conventional and within the ability of those skilled in the art, and so will not be further described.

The first step of the GPF correction involves connecting the bioimpedance transducer with a source of an electrically-generated sinusoidal impedance signal and then measuring the output from the transducer. The electrically-generated sinusoidal impedance signal has an amplitude of 0.1 Ohm to 0.2 Ohm with respect to a baseline, for example, 100 Ohm to 200 Ohm. Such a signal has been developed using a voltage-to-impedance converter consisting of a photoresistor, a photoemitter (photo diode), a power supply, and an analog-digital-analog (ADA) computer interface. The paired photoresistor and photoemitter are coupled inside a light-protected housing so that the photoresistor changes its impedance according to the photoemitter's light intensity. The ADA conversion process includes digital-to-analog conversion of the mathematically-modeled sinusoid with a frequency of 19 kHz and analog-to-digital conversion was a frequency of 100 Hz, with 12 bit resolution. Through the interface, the computer produces a set of test sinusoidal signals with frequencies in the range from 0 Hz to 75 Hz and records the responses of the transducer. The operation characteristics of the voltage-to-impedance converter include an input signal of 0 V to 5 V, an output signal of −0.1 Ohm to 0.1 Ohm with a baseline of 100 Ohm to 200 Ohm (as previously noted). The GPF characteristic H(f) of the transducer may then be calculated from the spectrums of the initial test signals and the resulting responses of the transducer and presented as a graph or stored in an ASCH or other memory file. The system uses the calculated GPF characteristic H(f) of the transducer to calculate the "restoring" R-filter. The GPF characteristic of such R-filter can be formally written as 1/H(f) in a certain frequency range. The R-filter also provides frequency bounds through low and high frequency filters to provide suppression of random low and high frequency interference (see FIG. 7). The filtration with the R-filter may be done in the frequency domain using a Fourier transform. It is preferable to use a Gaussian window with Fourier transform to eliminate the boundary effects of the recorded signal:

$$G(t) = \exp[-2(at/(2t))^2]$$

where 2T is a duration of recorded signal, t<T is a time, and "a" is a predefined constant preferably in the range of 2.5–3. Multiplication of the Fourier image of the recorded signal by the R-filter's GPF characteristics results in suppression of GPF distortions and additional filtration of the signal. Reverse Fourier transformation and division by the Gaussian window may also be employed. The same steps may be employed in the time domain without Fourier transformation. The signal after R-filtration is referred to as the "restored" signal, and this signal is used for further calculations.

It should also be noted at this time that the identified GPF characteristics of the ECG connection are processed to remove hardware artifacts from the ECG signal in a similar manner to that described above for the bioimpedance signal. GPF correction of both the ECG and bioimpedance signals promotes true correspondence of time intervals and event times between the two signals.

Figure 5A:
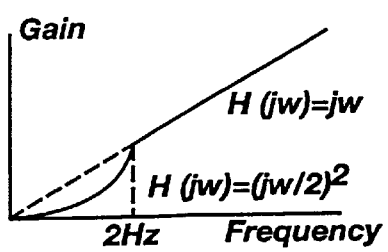
FIG. 5A is a graph of the gain versus frequency characteristics of an A-filter according to the invention employed for signal differentiations and harmonics suppression.

The next step in the bioimpedance signal processing is heart rate (HR) estimation. The present invention uses two ways to calculate HR. The ordinal way is to detect R-peaks on the ECG signal as described above and calculate R—R interval. The inverse value multiplied by 60 corresponds to heart rate. If ECG signal cannot be processed to detect R-peaks for some reason, the second way is used. In the second way, the power spectrum of the "restored" bioimpedance signal is calculated with discrete Fourier transform and used to estimate the patient's heart rate (HR). Very often a breath harmonic is the biggest one in the power spectrum of the bioimpedance signal. Consequently, it must be suppressed and the HR frequency response highlighted. A special transformation is used for this purpose. First, the power spectrum (PS) of the "restored" signal is multiplied with the gain-frequency characteristic of the A-filter (see FIG. 5A). This filter differentiates the signal and additionally suppresses harmonics below a certain frequency preferably selected at a range from 1 Hz to 3 Hz because breath wave harmonics commonly lie below 2 Hz and HR harmonics above 0.8 Hz. The power spectrum of clear cardio signal consists of repeated peas at frequencies HR, 2*HR, 3*HR, etc. Consequently, the following autoconvolution of the power spectrum will emphasize the heart rate harmonic:

$$AS1(f) = PSa(f) \cdot PSa(2f) \cdot PSa(3f)...$$

where ASI(i) is a result of the autoconvolution of the power spectrum and PSa(i) is the power of a given spectral line with frequency i which previously passed through the A-filter. It is preferable to have in the above product only the first three element PSa, because the higher the frequency is, the lower the signal-to-noise ratio. The computer system uses the autoconvolution of search for Mas, the maximum value of AS1(i) in the range of 0.6 Hz to 5 Hz. The frequency associated with Mas is regarded as an estimation of HR. The estimation of HR is then used in additional filtration (see FIG. 5C) and cardiocyclic-identification procedures.

Figure 5B:
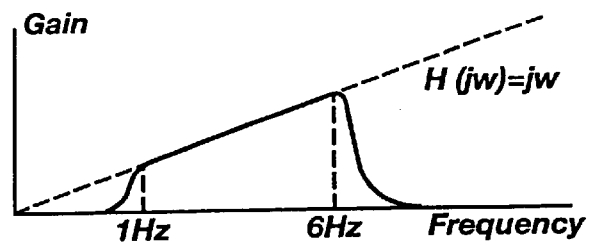
FIG. 5B is a graph of the gain versus frequency response of a B-filter as employed in the present invention to highlight the fronts of cardiocycles.
Figure 5C:
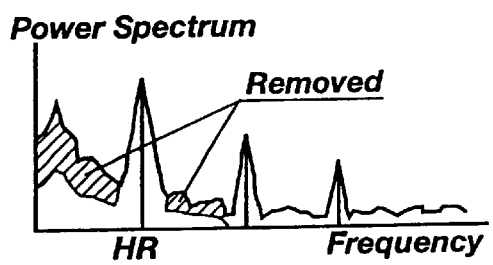
FIG. 5C is a graph of filtration employed to remove breath waves' power spectrum from the summary (breath and cardiowave) power spectrum in the present invention.

The aberrations in the bioimpedance signal caused by respiration must be removed to increase accuracy and to insure proper identification of the cardiocycles. Usually, breath frequency is less than heart rate frequency, but breath waves create a power spectrum which overlaps the lowest harmonics of the power spectrum created by the cardiocycles. So, it is impossible to remove the breath waves' power spectrum from the summary power spectrum entirely (see FIG. 5C). Cardiac strokes are a more stable, repetitive process in comparison with breath. Consequently, we can consider that their power spectrum consists of several narrow peaks. All power spectrum harmonics between main cardiowaves' spectrum lines are combination of lateral slopes of these main spectrum lines and a noise power spectrum. If these internal harmonics are decreased, noise is mainly suppressed, and cardiowaves only slightly. As subsequently noted, these ideas form the basis for the alogorithm for breath wave filtration. After estimation of heart rate (HR), as described above, the first and second harmonics of the cardiowaves' spectrum are determined. The local minimums at the power spectrum nearest to these spectrum peaks can be considered as their bounds. All harmonics below the lower bound of the second peak except for those within the first peak bounds are multiplied by a predetermined value less than 1 (as schematically shown in FIG. 5C). This results in elimination of breath wave amplitude, because the latter's power spectrum lies in the multiplied zone, but only slightly affects the cardiowaves.

The next step in bioimpedance signal processing is cardiocycle detection. The invention also uses two ways to do this. The first way is to place the cardiocycle borders according to QRS complexes positions in the ECG signal. If the ECG cannot be processed, the second way is used. In the second way, the "restored" signal as mentioned above is passed through the B-filter (FIG. 5B) to highlight the fronts of the cardiocycles. This is a differentiating filter with sinusoid-like frequency bounds. The pass band of the B-filter is adapted for frequency harmonics that produce a main contribution to cardiocycle front (preferably from 1 Hz to 6 Hz). The area between a local minimum and the next local maximum at the signal passed through the B-filter is regarded as a cycle front and described with a peak-to-peak change in time and a peak-to-peak change in amplitude. The computer system then generates a time-amplitude envelope by analyzing the first five (5) harmonics of the power spectrum generated by the signal after it passes through the B-filter. The cycle fronts are examined and certain ones are marked for further analysis if their peak-to-peak changes in time and peak-to-peak changes in amplitude are within the time-amplitude envelope. To increase the reliability of cardiocycles recognition, the computer system calculates mean and variance of peak-to-peak amplitudes for the selected region.

If the variance-per-mean ratio is less than a predetermined value, preferably 0.3, then all of the marked fronts are transmitted to the next stage which involves the arrangement of check points and the selection of defect free cardiocycles. In the alternative, if the variance-per-mean ratio is greater than a predetermined value, then additional analysis must be performed. The additional analysis comprises the following steps: (1) the regions under examination are separated into two groups according to their peak-to-peak amplitude: those above the mean value ("the upper group") and those below the mean value ("the lower group"); (ii) the means, M1 and M2, and variances or standard deviations, V1 and V2, are calculated for each group; (iii) the appropriate values are inserted into the following inequality for each group:

$$M2 + \alpha \cdot V2 < M1 - \alpha \cdot V1,$$

where a is a predetermined value, preferably 1.96, and V1 and V2 are standard deviations for the lower and upper groups respectively; and (iv) if the inequality holds true, then the regions in the upper group are taken to be the fronts of the cardiocycles and the regions in the lower group are eliminated from further consideration, otherwise all selected regions proceed to the next stage.

The computer system identifies certain check points in the time-differentiated bioimpedance signal to calculate the effective left ventricular ejection time, ELVET, as a preliminary step in determining heart stroke volume (SV).

The present invention uses ELVET, a term which represents only the left ventricular ejection time, rather than Kubicek's VET, a term which represents the combined left and right ventricular ejection times. It is known that the value of the time-differentiated impedance signal is proportional to peak aortic blood flow ejected by the left ventricle. Therefore, the most accurate calculation of SV requires that LVET be used. LVET is calculated from the following equation:

$$LVET = ELVET + LVPT,$$

where ELVET is the time between the moment the left ventricular valve opens (S-point) and the moment that it begins to close (T-point), and LVPT is the protodiastoly time (the time it takes for the left ventricular valve to close). LVPT is not readily detectable with hemodynamic monitoring means because the changes in blood flow are insignificant during the protodiastoly time. For this reason, the present invention uses the product of ELVET and $(dZ/dt)_{max}$, the maximum absolute value of the first chest impedance derivative with respect to time, to account for the lack of an LVPT measurement.

The calculation of ELVET requires an analysis of the curve generated by the graph of Y(x), time-derivative bioimpedance, plotted with respect to time (see FIG. 9). The computer system first finds a global maximum of time-derivative impedance, Y(x), over a given cardiocycle and designates it as point A. The computer system then traces back in time from the A-point to the point in time corresponding to the $S_a$-point on the ECG signal, and looks for abnormalities in the bioimpedance signal between those two points (see FIG. 12). The abnormalities of interest are: (1) dZ/dt zero crossing, (2) local minimum in dZ/dt, and (3) local maximum in the third derivative of the bioimpedance signal, $d^3Z/dt^3$. It there is no abnormality in the bioimpedance signal found in the time interval between points A and $S_a$, the cycle is considered defective and rejected from further consideration. If any abnormalities are found to the right of $S_b$, the abnormality closest to $S_h$ approached from the right is selected as the ejection start time, S. Otherwise, the abnormality closest of $S_h$ approached from the left is selected as the ejection start time, S. The usage of the ECG signal increases stability of the S recognition in complex cases.

To identify the end of ELVET, point T, the computer system first finds point $T_0$, which is taken to be either the first or the second local minimum after point A at the time differentiated bioimpedance signal, labeled as $T_1$ and $T_2$ respective (see FIG. 9). The computer system chooses between $T_1$ and $T_2$ after an analysis of the depth (amplitude) of the curve at each point. If depth of the second minimum is greater than a predetermined fractional value of the depth of the first minimum, then $T_2$ is selected as $T_0$. Otherwise, $T_1$ is used. To increase the stability of $T_0$ detection in noisy signals, the invention looks for the back or trailing edge of the T-wave in the ECG signal. The back edge of the T-wave is detected from the local maximum at ECG signal next to QRS complex up to the next local maximum at the graph of curvature of ECG signal versus time. If one of the points $T_1$ or $T_2$ is out of bounds of the T-wave's back, the other point is used as $T_0$ regardless of its amplitude. The "effective end" of the ventricular ejection, point T, is then identified as the nearest local minimum before point $T_0$ on the graph of the curve generated by the second derivative of Y(x). ELVET is calculated as the time distance between points S and T.

The inventive method of determining ELVET has been correlated to an ultrasound ELVET determination with a correlation coefficient of r=0.86. Kubicek's classic algorithm gives only a correlation of r=0.71. See FIG. 15 for a graphic depiction of the correlations of the classic versus the new methodology to the ideal. Consequently, and in contrast to Kubicek, left ventricular ejection time as measured by the inventive method is measured in substantial isolation from the right ventricular ejection time.

Normally, the point of the ejection start, S, coincides with the zero crossing of the time-differentiated (dZ/dt) bioimpedance signal (see FIG. 13), but this is not the case for seriously ill patients (see FIG. 14). For such patients the point of the ejection start is often placed at the "stair" or "abnormality" of the first front of the bioimpedance signal. This "stair" or "abnormality" characteristic (also termed a "prewave") of an ill patient is commonly referred to as left-right ventricular asynchromism.

For healthy patients, the impedance value at the beginning of QRS complex at ECG (Q-point), $Z_q$ is almost the same as the impedance value at the S-point, $Z_s$. This impedance difference is measured as $Z_{s-q}$, (see FIG. 13). However, for ill patients, $Z_{s-q}$ can be significant, (see FIG. 14). Where $Z_{s-q}$ is small, Kubicek's estimation of $\Delta Z = (dZ/dt)_{max} * VET$, is fairly accurate. For seriously ill patients exhibiting left-right ventricular asynchronism, however, the Kubicek equation generally underestimates $\Delta Z$. Thus, the premise of the "prewave" should be accounted for in making the calculation. This invention compensates for the inherent underestimation of $\Delta Z$ in ill patients by adding the bioimpedance difference between S and Q points, $Z_{s-q}$ to Kubicek's $\Delta Z$ estimation. By making this compensation, $\Delta Z$ is more accurately estimated, and the regression between bioimpedance and thermodilution cardiac output values is linearized. Thus, the computer system estimates $\Delta Z$ as $$\Delta Z = (dZ/dt)_{max} \cdot ELVET + Z_{s-q}$$

where $Z_{s-q}$ is the bioimpedance difference S and Q points.

After the computer system arranges all check points, it eliminates cardiocycles with certain aberrations. Fuzzy logic and fitness algorithms may be employed in this procedure. Several criteria are used for this purpose. The computer system first confirms that the time distances between the points described above for each cardiocycle (e.g., point A, point T, Point S) do not exceed certain bounds. It also verifies that the amplitude difference between the start and the end of the cardiocycle do not exceed a predefined value. The amplitude change between the start and end of the cardiocycle must not exceed a predefined percentage of the maximum amplitude over that cardiocycle. Furthermore, the ratio of the time-derivative bioimpedance signal amplitude at point A to the time-derivative bioimpedance signal at point T must be greater than a predetermined value; that is:

$$Y(A)/Y(T) > c,$$

where Y(A) and Y(T) are the values of the time-derivative bioimpedance signal at points A and T respectively, and "c" is the predetermined value. All cardiocycles that pass this stage are considered as "not very bad." The computer system then checks for the "neighbors criterion" to eliminate the effect of random noise in the bioimpedance signal. A three-dimensional "nearness" vector with elements (A1$i$, A2$i$, A3$i$) is calculated for each pair of cardiocycles in a 10 second time block. The individual elements of the nearness vector are determined using the following equations:

$$A1_i = [Y(A_i) - Y(A_j)]/[Y(A_i) + Y(A_j)],$$

$$A2_i = (ST_i - ST_j)/(ST_i + ST_j),$$

and $$A3_i = \frac{([Y(B_i) - Y(T_i)] - [Y(B_j) - Y(T_j)])}{([Y(B_i) - Y(T_i)] + [Y(B_j) - Y(T_j)])},$$

where Y(x) is time-differentiated bioimpedance at a given point x, A, T, and B are check point positions in each cardiocycle (see FIG. 9); ST is the time between points S and T; and i and j are different cardiocycles. The computer system compares all of the calculated nearness vectors and eliminates those cardiocycles wherein the amplitudes of the nearness vectors exceeds certain thresholds. The comparison is made using a two-threshold analysis. If the nearness vector amplitude of two cardiocycles is less than a first predefined value, L1, the similarity is considered "good." If the similarity fails to be considered "good" (the similarity exceeds L1), but is still less than second predefined value, L2, it is considered as "acceptable." If the similarity fails to be considered "acceptable" for the 10 second block of data, the computer system compares the tested cardiocycle with up to 50 previous "not very bad" cycles. If there is still no cycle similar to the one being considered, the cycle under consideration is regarded as noisy, and is rejected. If the amount of "good" cardiocycles is big enough, all "acceptable" cardiocycles also rejected from the final calculation. This methodology increases the stability of the calculations at the highest noise levels, as only "good" cardiocycles are used in the final calculations.

After the bioimpedance signal processing is complete, the computer system performs the final calculation of hemodynamic parameters, together with means and variances for the entire data block. Heart Rate (HR) and Heart Stroke Volume (SV) are recalculated using the respective methods described above, except that the processed bioimpedance signal is used instead of the unprocessed bioimpedance signal. Cardiac Output (CO) is calculated as the product of HR and SV; that is:

$$CO = SV \cdot HR.$$

Figure 6A:
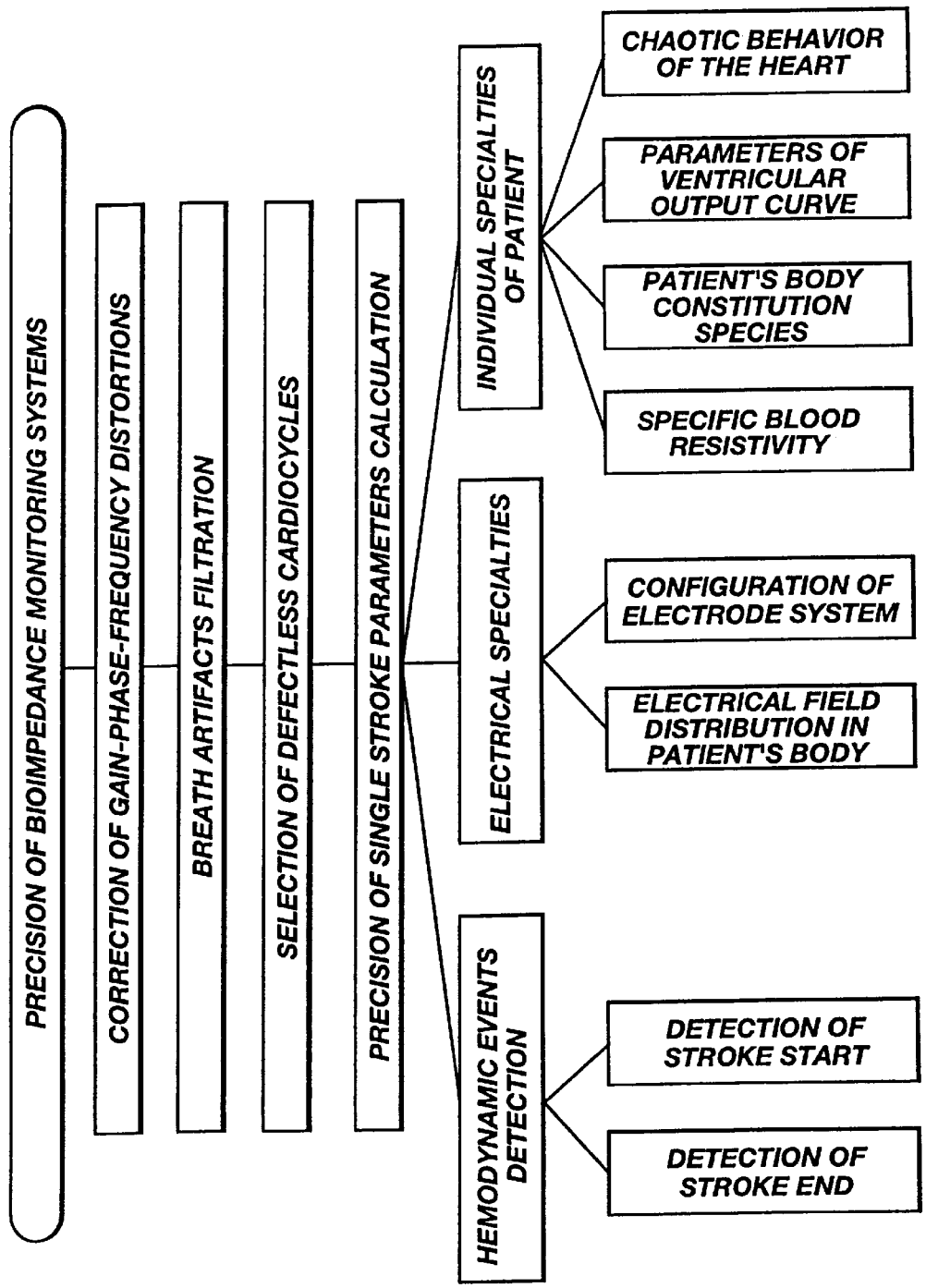
FIG. 6A is a branch chart of the methodology of the present invention.
Figure 6B:
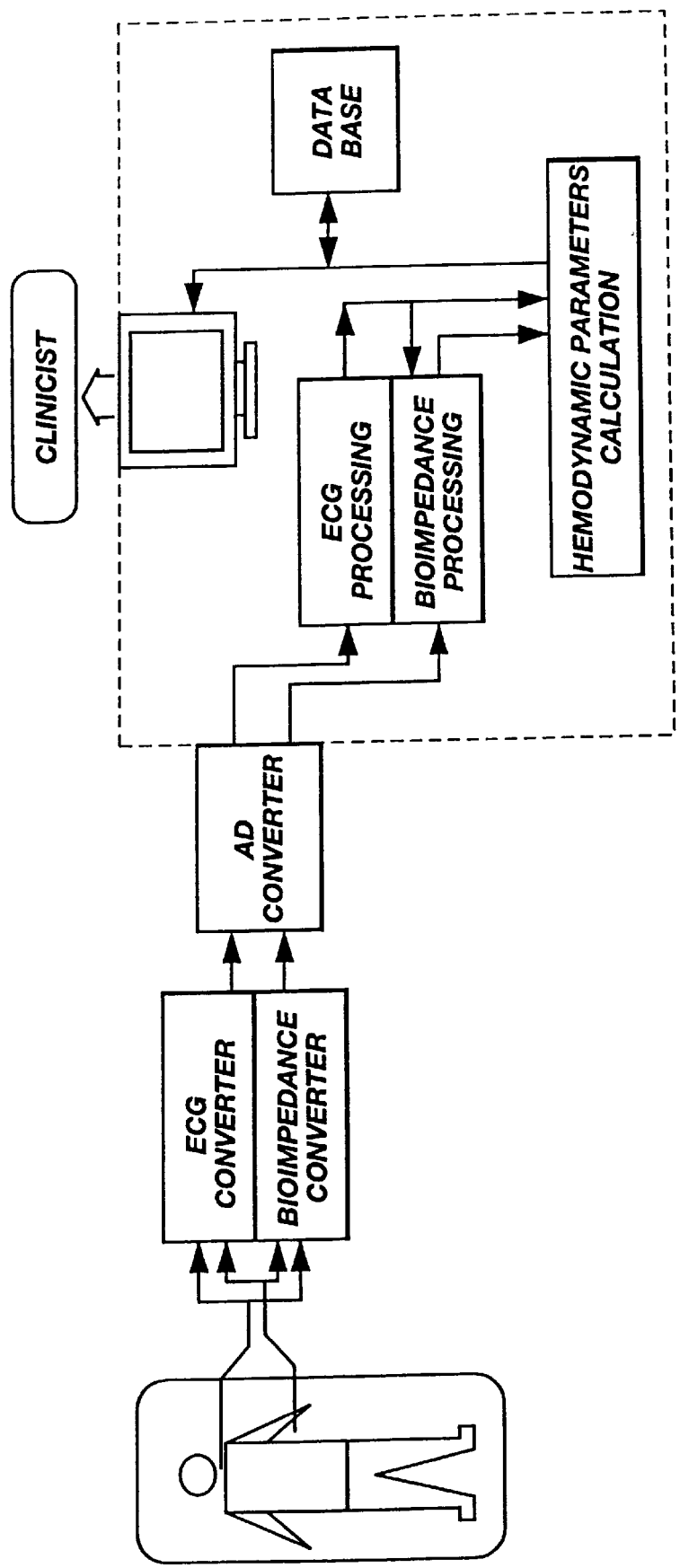
FIG. 6B is a flow chart of signal processing and depicting the apparatus employed in performing the method of the present invention.

An outline of the general methodology of the present invention is set forth in FIG. 6A. FIG. 6B depicts the flow chart of signal processing in the present invention.

While the present invention has been described in terms of a preferred embodiment, those of ordinary skill in the art will recognize and appreciate that it is not so limited. Many additions, deletions and modifications to the disclosed embodiment may be made without departing from the scope of the invention as hereinafter claimed.

What is claimed is:

1. A method for processing a bioimpedance signal and electrocardiogram for deriving heart rate, heart stroke volume, and cardiac output comprising:

registering gain-phase-frequency (GPF) characteristics of input analog devices for measuring bioimpedance;

registering gain-phase-frequency (GPF) characteristics of input analog devices for measuring electrocardiogram;

measuring bioimpedance as a function of time over a given time period with said input analog devices for measuring bioimpedance and generating a bioimpedance signal;

measuring electrocardiogram as a function of time over said given time period with said input analog devices for measuring electrocardiogram and generating an electrocardiogram (ECG) signal;

correcting the bioimpedance signal for distortions based on the GPF characteristics previously registered;

correcting the electrocardiogram signal for distortions based on the GPF characteristics previously registered;

determining valid QRS complexes associated with each cardiocycle of said electrocardiogram signal in the given time period;

locating check-points on said valid QRS complexes;

processing one of said ECG signal and said corrected bioimpedance signal to estimate heart rate;

time-differentiating the corrected bioimpedance signal;

determining check-points for each said cardiocycle of the time-differentiated bioimpedance signal in the given time period;

determining effective left ventricular ejection time (ELVET) using said time differentiated bioimpedance check-points in relation to said corresponding QRS check-points;

determining a novel correction factor $Z_{s-q}$ using said time differentiated bioimpedance check-points in relation to said corresponding QRS check-points;

calculating stroke volume as a function of said ELVET, maximum time-differentiated bioimpedance $(dZ/dt)_{max}$, specific blood resistivity (P), distance (L) between two bioimpedance voltage sensing electrodes of the bioimpedance analog input device, baseline bioimpedance ($Z_0$), said correction factor $Z_{s-q}$, and a novel scale factor (K); and calculating cardiac output by multiplying said stroke volume by said heart rate.

2. The method of claim 1, wherein said registering gain-phase-frequency (GPF) characteristics of said bioimpedance input analog devices comprises determining phase-frequency and gain-frequency characteristics of a transducer employed in detection of said bioimpedance prior to use thereof in said detection.

3. The method of claim 1, wherein said correcting of measured bioimpedance signal comprises digitally filtering and phase correcting said measured bioimpedance to remove distortion in the output of said transducer.

4. The method of claim 1, wherein said registering gain-phase-frequency (GPF) characteristics of said electrocardiogram input analog devices comprise determining phase-frequency and gain-frequency characteristics of a transducer employed in detection of said electrocardiogram prior to use thereof in said detection.

5. The method of claim 1, wherein said correcting of measured electrocardiogram signal comprises digitally filtering and phase correcting said measured electrocardiogram to remove distortion in the output of said transducer.

6. The method of claim 1, wherein said estimating heart rate comprises using a power spectrum of the bioimpedance signal, and an auto-convolution function of the said power spectrum.

7. The method of claim 1, wherein said estimating heart rate comprises processing the electrocardiogram signal.

8. The method of claim 3, wherein said correcting of measured bioimpedance signal further consists of suppressing breath waves to remove undesired power spectra components and generate a bioimpedance signal of restored shape.

9. The method of claim 1, wherein said determining valid QRS complexes comprises determining a distribution of all peaks measured in an electrocardiogram over a period of time (from the front ($E_1$) and back ($E_2$) amplitudes of the peaks, calculating the ($E_1$, $E_2$) amplitude envelope and rejecting all peaks outside the envelope.

10. The method of claim 4, wherein said determining transducer phase-frequency and gain-frequency characteristics comprises:
generating a high precision sinusoidal impedance signal with peak-to-peak impedance of approximately 0.2 Ohms and baseline impedance of approximately 100 Ohms to 200 Ohms;
connecting said sinusoidal impedance signal to said transducer;
measuring the output from said transducer; and
calculating a gain-phase-frequency characteristic, H(f), of the transducer in a predefined frequency range.

11. The method of claim 10, further comprising generating said high precision sinusoidal impedance signal using a voltage-to-impedance converter including a photoresistor, a photoemitter, a power supply and an analog-to-digital-to analog computer interface.

12. The method of claim 11, further comprising producing through said interface a set of test signals with predefined amplitude and frequency range, detecting an output signal from said transducer, and analyzing said output signal to determine said phase-frequency and said gain-frequency characteristics.

13. The method of claim 10, further comprising employing posterior signal processing to correct linear gain-phase-frequency distortions by converting real operating characteristics of the transducer to predefined characteristics, wherein phase shift is zeroed and gain is assumed to be constant in a predefined frequency range.

14. A method of heart rate estimation, comprising:
calculation of a power spectrum of a bioimpedance signal;
multiplication of said power spectrum by a selected amplitude-frequency function to differentiate the signal and suppress breath harmonics;
autoconvoluting the resulting power spectrum according to the formula $$AS1(f)=PSa(f) \cdot PSa(2f) \cdot PSa(3f) \ldots ;$$

and
determining a maximum amplitude value of autoconvolution in a predefined frequency range as an estimation of heart rate.

15. A method for determining cardiocycles, comprising:
filtering a bioimpedance signal to emphasize fronts of cardiocycles;
calculating a time-amplitude envelope of said cardiocycles by analyzing the first five harmonics of the power spectrum of said bioimpedance signal after said filtration;
selecting said cardiocycle fronts by comparison with said calculated time-amplitude envelope; and
rejecting erroneously-detected fronts.

16. A method of selecting valid cardiocycles from corrected bioimpedance signals to eliminate cardiocycles having interference artifacts, comprising:
detecting time and amplitude relations referencing check points within individuals of a plurality of cardiocycles;
comparing said time and amplitude relations between individuals of a said plurality of cardiocycles; and
further examining selected cardiocycles which exhibit the presence of artifacts according to a plurality of comparison criteria.

17. The method of claim 16, further comprising:
constructing a multi-dimensional vector for each selected cardiocycle;
comparing said multi-dimensional vector with such vectors for other cardiocycles and;
rejecting the cardiocycles with vectors having no neighboring vectors when compared to last 50 valid cardiocycles and other candidate cardiocycles.

18. A method of deriving effective left ventricular ejection time from measured bioimpedance signal and measured electrocardiogram signal, comprising:
filtering said measured bioimpedance signal and suppressing breath waves therein;
filtering said measured electrocardiogram signal;
detecting a valid cardiocycle;
calculating the time-derivative of said bioimpedance signal Y(x);
determining the maximum value of the time-derivative $(dZ/dt)_{max}$,
determining effective ejection start time (S-point);
determining effective ejection end time (T-point); and
calculating effective left ventricular ejection time (ELVET) as change in time between effective ejection start time and end time.

19. The method of claim 18, wherein determining effective ejection start time comprises:
determining the global maximum for a given valid cardiocycle of a time-differentiated bioimpedance signal and designating said maximum as point A;
tracing back in time from corresponding point A on electrocardiogram to point $S_1$;
looking for abnormalities in the bioimpedance signal between points A and $S_a$;
if there are no said abnormalities, then the cardiocycle is rejected as noisy;
if there are any said abnormalities the one closest to point $S_b$ approached from the right is selected as the ejection start time S;
otherwise the abnormality nearest $S_b$ approached from the left is selected as the ejection start time S.

20. The method of claim 19, wherein determining effective ejection end time comprises:
determining the first ($T_1$) and second ($T_2$) local minimums at the time-differentiated bioimpedance signal after point A;
analyzing the depth of the signal curve at each of the first ($T_1$) and second ($T_2$) local minimums;
if the depth of the second ($T_2$) minimum is greater than a predetermined fractional value of the depth of the first ($T_1$) minimum, selecting the second minimum ($T_2$) as $T_0$;

otherwise, selecting $T_1$ as $T_0$; and identifying the T-point as the nearest local minimum before point $T_0$ on the graph of the curve generated by the second derivative of $Y(x)$.

21. The method of claim 20, further comprising, after identifying $T_1$ and $T_2$ and before identifying the T-point and regardless of relative amplitudes of $T_1$ and $T_2$;

detecting a back edge of a T-wave in the electron cardiogram signal;

determining if $T_1$ or $T_2$ is out of bounds of the back of the T-wave; and if so, selecting the one of $T_1$ or $T_2$ which is not out of bounds as $T_0$.

22. In the method of claim 19, abnormalities are selected from the group comprising: dZ/dt zero crossing (Q-point), local minimum in dZ/dt, and local maximum in the third time-derivative of the bioimpedance signal, $d^3Z/dt^3$.

23. A method of determining stroke volume for a patient, comprising:

determining specific blood resistivity P;

measuring a distance L between two bioimpedance electrodes applied to the patient;

determining the base thoracic impedance $Z_0$;

determining ELVET;

determining $\Delta Z$, impedance changes due to blood influx;

and calculating stroke volume SV according to the equation $$SV = K \cdot P \cdot (L/Z_n)^2 \cdot \Delta Z$$

where K is a novel scale factor related to body composition of the patient.

24. The method of claim 23, further comprising calculating K as $$K = K_n - K_s \cdot (SCHEST/(H^e2 \cdot W^e3)),$$

where $$SCHEST = (PSCHEST^2 + (PNECK \cdot PCHEST) + PNECK^2)/12\pi.$$

25. The method of claim 24, wherein $K_0$, $K_1$, $K_2$, $K_3$ are gender and age dependent and lie in ranges of $$K_n \in [1-4]; K_s \in [3-16]; K_0 \in [0-1]; K_r \in [0.1-2].$$

26. A method of claim 23, wherein determining $\Delta Z$ comprises:

locating the start of QRS complex of an ECG signal and labelling it point Q;

determining the impedance at point S, $Z_s$;

determining the impedance at point Q, $Z_q$;

calculating the impedance difference $Z_{s-q}$ between points S and Q;

estimating $\Delta Z$ according to the formula $$\Delta Z = (dZ/dt)_{rc} \cdot ELVET + Z.$$

27. A method of breath wave suppression for a bioimpedance signal, comprising:

calculating the Fourier transform of the signal;

locating the first and second frequency harmonics of cardiocycles in the calculated spectrum of the signal;

estimating the width of each of the harmonics;

suppressing frequency harmonics below the lower bound of the second harmonic except for harmonics within the bounds of the first frequency harmonic; and calculating the inverted Fourier transform of the signal.

28. A system for non-invasive monitoring of hemodynamic parameters using detected thoracic bioimpedance and electrocardiogram indications, comprising:

an electrode arrangement adapted for detecting thoracic bioimpedance and electrocardiogram indications of a patient to provide analog signals representative of said indications;

means for correcting errors associated with said analog signals;

means for converting said corrected analog signals to digital signals;

means for processing said digital signals to effectuate at least one of:

estimation of heart rate;

suppression of breath artifact in said bioimpedance signal;

cardiocycle recognition;

arrangement of check points; and selection of cardiocycles devoid of artifact.

29. The system of claim 28, wherein said means for correcting errors associated with said analog signals comprises:

means for registering gain-phase-frequency (GPF) characteristics of input analog devices for measuring bioimpedance;

means for registering gain-phase-frequency (GPF) characteristics of input analog devices for measuring electrocardiogram;

means for measuring bioimpedance as a function of time over a given time period with said bioimpedance input analog devices and generating a bioimpedance signal;

means for measuring electrocardiogram as a function of time over said given time period with said electrocardiogram input analog devices and generating an electrocardiogram (ECG) signal;

means for correcting the bioimpedance signal for distortions based on the GPF characteristics previously registered; and means for correcting the electrocardiogram signal for distortions based on the GPF characteristics previously registered.

30. The system of claim 29, wherein said means for processing comprises:

means for determining valid QRS complexes associated with each cardiocycle of said electrocardiogram signal in the given time period;

means for locating check-points on said valid QRS complexes;

means for processing one of said ECG signal and said corrected bioimpedance signal to estimate heart rate;

means for time-differentiating the corrected bioimpedance signal;

means for determining check-points for each said cardiocycle of the time-differentiated bioimpedance signal in the given time period;

determining effective left ventricular ejection time (ELVET) using said time differentiated bioimpedance check-points in relation to said corresponding QRS check-points;

determining a novel correction factor $Z_{s-q}$ using said time differentiated bioimpedance check-points in relation to said corresponding QRS check-points.

31. The system of claim 29, further comprising means for calculation of stroke volume adaptive to the patient's constitution, sex and exhibited features of cardiac stroke waveform.

32. The system of claim 31, wherein said means for calculation of stroke volume comprise:

means for calculating stroke volume as a function of said ELVET, maximum time-differentiated bioimpedance $(dZ/dt)_{max}$, specific blood resistivity (P), distance (L) between two bioimpedance voltage sensing electrodes of the bioimpedance analog input device, baseline bioimpedance ($Z_0$), said correction factor $Z_{s-q}$, and a novel scale factor (K).

33. The system of claim 32, further comprising means for calculation of cardiac output from said calculated stroke volume by said estimated heart rate.

34. The system of claim 29, wherein said means for registering gain-phase-frequency (GPF) characteristics of said bioimpedance input analog devices comprises means for determining phase-frequency and gain-frequency characteristics of a transducer employed in detection of said bioimpedance prior to use thereof in said detection.

35. The system of claim 29, wherein said means for correcting of measured bioimpedance signal comprises means for digitally filtering and phase correcting said measured bioimpedance to remove distortion in the output of said transducer.

36. The system of claim 29, wherein said means for registering gain-phase-frequency (GPF) characteristics of said electrocardiogram input analog devices comprises means for determining phase-frequency and gain-frequency characteristics of a transducer employed in detection of said electrocardiogram prior to use thereof in said detection.

37. The system of claim 29, wherein said means for correcting measured electrocardiogram signal comprises means for digitally filtering and phase correcting said measured electrocardiogram to remove distortion in the output of said transducer.

38. The system of claim 28, wherein said processing means is adapted to estimate heart rate using a power spectrum of the bioimpedance signal, and an auto-convolution function of the said power spectrum.

39. The system of claim 28, wherein said estimating heart rate comprises processing the electrocardiogram signal.

40. The system of claim 29, wherein said means for correcting measured bioimpedance signal is adapted to suppress breath waves to remove undesired power spectra components and generate a bioimpedance signal of restored shape.

41. The system of claim 30, wherein said means for determining valid QRS complexes is adapted to determine a distribution of all peaks measured in an electrocardiogram over a period of time (from the front ($E_1$) and back ($E_2$) amplitudes of the peaks, calculating the ($E_1$, $E_2$) amplitude envelope and rejecting all peaks outside the envelope.

42. The system of claim 34, wherein said means for determining transducer phase-frequency and gain-frequency characteristics is adapted to:

generate a high precision sinusoidal impedance signal with peak-to-peak impedance of approximately 0.2 Ohms and baseline impedance of approximately 100 Ohms to 200 Ohms;

connect said sinusoidal impedance signal to said transducer;

measure the output from said transducer; and calculate a gain-phase-frequency characteristic, H(f), of the transducer in a predefined frequency range.

43. The system of claim 42, further comprising means for generating said high precision sinusoidal impedance signal using a voltage-to-impedance converter including a photo-resistor; a photoemitter, a power supply and an analog-to-digital-to analog computer interface.

44. The system of claim 43, further comprising means for producing through said interface a set of test signals with predefined amplitude and frequency range, detecting an output signal from said transducer, and analyzing said output signal to determine said phase-frequency and said gain-frequency characteristics.

45. The system of claim 42, further comprising means for employing posterior signal processing to correct linear gain-phase-frequency distortions by converting real operating characteristics of the transducer to predefined characteristics, wherein phase shift is zeroed and gain is assumed to be constant in a predefined frequency range.

46. The system of claim 28, wherein the processing means is adapted to estimate heart rate by:

calculation of a power spectrum of a bioimpedance signal;

multiplication of said power spectrum by a selected amplitude-frequency function to differentiate the signal and suppress breath harmonics;

autoconvoluting the resulting power spectrum according to the formula $AS1(f)=PSa(f) \cdot PSa(2f) \cdot PSa(3f) \ldots$ and determining a maximum amplitude value of autoconvolution in a predefined frequency range as an estimation of heart rate.

47. The system of claim 28, wherein the processing means is adapted to recognize cardiocycles by:

filtering a bioimpedance signal to emphasize fronts of cardiocycles;

calculating a time-amplitude envelope of said cardiocycles by analyzing the first five harmonics of the power spectrum of said bioimpedance signal after said filtration;

selecting said cardiocycle fronts by comparison with said calculated time-amplitude envelope; and rejecting erroneously detected fronts.

48. The system of claim 28, wherein said processing means is adapted to select valid cardiocycles from corrected bioimpedance signals to eliminate cardiocycles having interference artifacts by:

detecting time and amplitude relations referencing check points within individuals of a plurality of cardiocycles;

comparing said time and amplitude relations between individuals of a said plurality of cardiocycles; and further examining selected cardiocycles which exhibit the presence of artifacts according to a plurality of comparison criteria.

49. The system of claim 48, wherein said processing means is further adapted to:

construct a multi-dimensional vector for each selected cardiocycle;

compare said multi-dimensional vector with such vectors for other cardiocycles and;

reject the cardiocycles with vectors having no neighboring vectors when compared to last 50 valid cardiocycles and other candidate cardiocycles.

50. The system of claim 30, wherein said processing means is adapted to derive effective left ventricular ejection time from said bioimpedance signal and said electrocardiogram signal by:

filtering said measured bioimpedance signal and suppressing breath waves therein;

filtering said measured electrocardiogram signal;

detecting a valid cardiocycle;

calculating the time-derivative of said bioimpedance signal $Y(x)$;

determining the maximum value of the time-derivative $(dZ/dt)_{max}$;

determining effective ejection start time (S-point);

determining effective ejection end time (T-point); and calculating effective left ventricular ejection time (ELVET) as change in time between effective ejection start time and end time.

51. The system of claim 50, wherein determining effective ejection start time is effected by:

determining the global maximum for a given valid cardiocycle of a time-differentiated bioimpedance signal and designating said maximum as point A;

tracing back in time from corresponding point A on electrocardiogram to point $S_a$;

looking for abnormalities in the bioimpedance signal between points A and $S_a$;

if there are no said abnormalities, then the cardiocycle is rejected as noisy;

if there are any said abnormalities the one closest to point $S_b$ approached from the right is selected as the ejection start time S;

otherwise the abnormality nearest $S_b$ approached from the left is selected as the ejection start time S.

52. The system of claim 51, wherein determining effective ejection end time is effected by:

determining the first ($T_1$) and second ($T_2$) local minimums at the time-differentiated bioimpedance signal after point A;

analyzing the depth of the signal curve at each of the first ($T_1$) and second ($T_2$) local minimums;

if the depth of the second ($T_2$) minimum is greater than a predetermined fractional value of the depth of the first ($T_1$) minimum, selecting the second minimum ($T_2$) as $T_0$; otherwise, selecting $T_1$ as $T_0$; and identifying the T-point as the nearest local minimum before point $T_0$ on the graph of the curve generated by the second derivative of $Y(x)$.

53. The system of claim 52, wherein said processing means is further adapted to, after identifying $T_1$ and $T_2$ and before identifying the T-point and regardless of relative amplitudes of $T_1$ and $T_2$;

detect a back edge of a T-wave in the electron cardiogram signal;

determine if $T_1$ or $T_2$ is out of bounds of the back of the T-wave; and if so, select the one of $T_1$ or $T_2$ which is not out of bounds as $T_0$.

54. The system of claim 51, wherein abnormalities are selected from the group comprising: $dZ/dt$ zero crossing (Q-point), local minimum in $dZ/dt$, and local maximum in the third time-derivative of the bioimpedance signal, $d^3Z/dt^3$.

55. The system of claim 31, wherein said processing means is adapted to determine stroke volume for said patient by:

determining specific blood resistivity P;

measuring a distance L between two bioimpedance electrodes applied to said patient;

determining the base thoracic impedance $Z_0$;

determining ELVET;

determining $\Delta Z$, impedance changes due to blood influx;

and calculating stroke volume SV according to the equation $$SV = K \cdot P \cdot (L/Z_n)^2 \cdot \Delta Z$$

where K is a novel scale factor related to body composition of said patient.

56. The system of claim 55, wherein:

$$K = K_n - K_\theta \cdot (SCHEST/(H^{r2} \cdot W^{r3})),$$

where $$SCHEST = (PSCHEST^2 + (PNECK \cdot PCHEST) + PNECK^2)/12\pi.$$

57. The system of claim 56, wherein $K_0$, $K_1$, $K_2$, $K_3$ are gender and age dependent and lie in ranges of $$K_n \in [1-4];\ K_3 \in [3-16];\ K_0 \in [0-1];\ K_1 \in [0.1-2].$$

58. A system of claim 55, wherein $\Delta Z$ is determined by:

locating the start of QRS complex of an ECG signal and labeling it point Q;

determining the impedance at point S, $Z_s$;

determining the impedance at point Q, $Z_q$;

calculating the impedance difference $Z_{s-q}$ between points S and Q;

estimating $\Delta Z$ according to the formula $$\Delta Z = (dZ/dt)_{rc} \cdot ELVET + Z.$$

59. The system of claim 28, wherein said processing means is adapted to suppress breath artifact by:

calculating the Fourier transform of the signal;

locating the first and second frequency harmonics of cardiocycles in the calculated spectrum of the signal;

estimating the width of each of the harmonics;

suppressing frequency harmonics below the lower bound of the second harmonic except for harmonics within the bounds of the first frequency harmonic; and calculating the inverted Fourier transform of the signal.

60. The system of claim 59, wherein said electrode arrangement comprises:

an upper influencing electrode placed on the subject's head;

a lower influencing electrode placed on the left lower extremity of the subject;

an upper pair of detecting electrodes placed on the subject's neck; and a lower pair of detecting electrodes placed on the trunk of the subject.

61. The system of claim 60, wherein the electrode arrangement placement geometry further comprises:

an upper influencing electrode placed on the subject's forehead;

a lower influencing electrode placed in the general area of the subject's left knee;

a pair of upper detecting electrodes placed on the subject's neck; and a pair of lower detecting electrodes placed laterally on opposite sides of the subject's chest.

62. The system of claim 61, wherein said upper influencing electrode comprises a spot electrode for orientation on vertical and horizontal center lines of said subject's forehead.

63. The system of claim 60, wherein said lower influencing electrode comprises a spot electrode, the placement of which satisfies the relationship L<5R, where L is the vertical distance between said upper and said lower influencing electrodes and R is the radius of said subject's chest.

64. The system of claim 60, wherein said upper detecting electrodes comprises a pair of spot electrodes oriented symmetrically on opposite sides of said subject's neck along a horizontal line approximately 4 centimeters above the base of said subject's neck.

65. The system of claim 61, wherein said lower detecting electrodes further comprise a pair of electrode assemblies, each assembly providing contact surface area between about 12 square centimeters and about 30 square centimeters oriented laterally on opposite sides of said subject's chest at approximately xiphoid process level.

66. The system of claim 65, wherein each assembly further comprises four spot electrodes, wherein each spot electrode comprises approximately 4 square centimeters contact surface area with each said spot electrode centered at corners of a square with sides measuring 5 centimeters, and all 4 spot electrodes of said assembly electrically connected to each other.

67. The system of claim 66, wherein the top spot electrodes of each assembly lie on the xiphoid process level of the subject.

* * * * *